United States Patent [19]

Streissle et al.

[11] Patent Number: 4,564,622
[45] Date of Patent: Jan. 14, 1986

[54] TRIAZOLE DERIVATIVE AS AN ANTIVIRAL AGENT

[75] Inventors: Gert Streissle, Wuppertal; Manfred Plempel; Arnold Paessens, both of Haan; Graham Holmwood, Wuppertal; Karl H. Büchel, Burscheid, all of Fed. Rep. of Germany

[73] Assignee: Bayer Aktiengesellschaft, Leverkusen, Fed. Rep. of Germany

[21] Appl. No.: 728,061

[22] Filed: Apr. 29, 1985

Related U.S. Application Data

[63] Continuation of Ser. No. 536,409, Sep. 27, 1983, abandoned.

[30] Foreign Application Priority Data

Oct. 21, 1982 [DE] Fed. Rep. of Germany ....... 3238903

[51] Int. Cl.$^4$ .............................................. A61K 31/41
[52] U.S. Cl. ..................................... 514/383; 514/934
[58] Field of Search ......................................... 514/383

[56] References Cited

U.S. PATENT DOCUMENTS 4,086,351 4/1978 Balasubramonyan et al. ..... 424/267

FOREIGN PATENT DOCUMENTS 3018865 11/1981 Fed. Rep. of Germany .

OTHER PUBLICATIONS

Physicians' Desk Reference, 35th Ed., Charles J. Baker Jr., Publisher (Medical Economics Co., Oradell, N.J.), pp. 886–887, 1392–1393, (1981).

Primary Examiner—Allen J. Robinson
Attorney, Agent, or Firm—Sprung, Horn, Kramer & Woods

[57] ABSTRACT

The invention relates to 2-(4-chlorophenoxymethyl)-3,3-dimethyl-1-(1,2,4-triazol-1-yl)-2-butanol and its use for treating herpes viral infections.

5 Claims, No Drawings

TRIAZOLE DERIVATIVE AS AN ANTIVIRAL AGENT

This is a continuation of application Ser. No. 536,409, filed Sept. 27, 1983 (now abandoned).

The present invention relates to an antiviral agent which contains the known 2-(4-chlorophenoxymethyl)-3,3-dimethyl-1-(1,2,4-triazol-1-yl)-2-butanol as the active compound.

It has been found that the known 2-(4-chlorophenoxymethyl)-3,3-dimethyl-1-(1,2,4-triazol-1-yl)-2-butanol of the formula (I)

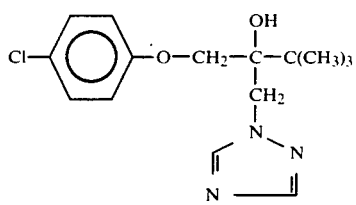

and its physiologically tolerated acid addition salts have strong antiviral effects.

Surprisingly, 2-(4-chlorophenoxymethyl)-3,3-dimethyl-1-(1,2,4-triazol-1-yl)-2-butanol of the formula (I) exhibits, in addition to a very good antimycotic effectiveness, a better antiviral effectiveness than the benzimidazole derivatives known from the state of the art, such as, in particular, 2(α-hydroxybenzyl)benzimidazole. The use of the compound of the formula (I) according to the invention thus represents an enrichment of pharmacy.

The active compound to be used according to the invention and its antimycotic effectiveness have already been disclosed (compare DE-OS (German Published Specification) No. 3,018,865).

The compound of the formula (I) according to the invention exhibits, as already mentioned, strong antiviral effects. These effects are particularly pronounced on lipid-containing viruses, such as, for example, herpes viruses.

Examples which can be mentioned of areas of indication in human medicine are: *Herpes labialis, Herpes genitalis, Keratoconjunctivitis herpetica,* varicella (chickenpox), *Herpes zoster (shingles), mononucleosis and infections with cytomegalovirus; warts caused by viruses. Specifically in veterinary medicine infections with pseudorabies virus (cattle, pigs), rhinotracheitis virus (cattle), rhinopneumonitis virus (horses) and Marek virus (chickens).*

The present invention includes pharmaceutical preparations which in addition to non-toxic, inert pharmaceutically suitable excipients contain the active compound according to the invention or which consist of the active compound according to the invention, and processes for the production of these preparations.

The present invention also includes pharmaceutical preparations in dosage units. This means that the preparations are in the form of individual parts, for example tablets, dragees, capsules, pills, suppositories and ampoules, of which the content of active substance corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Preferred pharmaceutical preparations which may be mentioned are tablets, dragees, capsules, pills, granules, suppositories, solutions, suspensions and emulsions, pastes, ointments, gels, creams, lotions, powders and sprays.

Tablets, dragees, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerine, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound only, or preferentially, in a certain part of the intestinal tract, optionally in a delayed manner, examples of embedding compositions which can be used being polymeric substances and waxes.

The active compound optionally together with one or more of the above mentioned excipients, can also be in a micro-encapsulated form.

Suppositories can contain, in addition to the active compound, the customary water-soluble or water-insoluble excipients, for example polyethylene glycols, fats, for example cacao fat, and higher esters (for example $C_{14}$-alcohol with $C_{16}$-fatty acid) or mixtures of these substances. The higher esters are preferably made from higher alkanols or alkenols and higher carboxylic acids which are alkane- or alkene-carboxylic acids.

Ointments, pastes, creams and gels can contain the customary excipients in addition to the active compound, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain the customary excipients in addition to the active compound, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottenseed oil, groundnut oil, maize germ oil, olive oil, castor oil and sesame oil, glycerine, glycerine-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain the customary excipients in addition to the active compound, such as liquid diluents, for example water, ethyl alcohol or propylene glycol, suspending agents, for example ethoxylated isostearyl alcohols, polyoxyethylene sorbitol esters and sorbitane esters, microcrystalline cellulose, aluminium metahydroxide, bentonite, agar-agar and tragacanth or mixtures of these substances.

The formulation forms mentioned can also contain dyestuffs, preservatives and additives which improve the odour and flavour, for example peppermint oil and eucalyptus oil, and sweeteners, for example saccharin.

The therapeutically active compound should preferably be present in the above mentioned pharmaceutical preparations in a concentration of about 0.01 to 99.5 percent by weight of the total mixture. Preferred concentrations are 0.1–50% for topical application, 0.5–50% for oral application, 0.01–10% for intraveneous application and 0.05–10% for other parenteral applications.

The above mentioned pharmaceutical preparations can also contain other pharmaceutical active compounds in addition to the active compound according to the invention.

The above mentioned pharmaceutical preparations are manufactured in the usual manner according to known methods, for example by mixing the active compound with the excipient or excipients.

The present invention also includes the use of the active compound according to the invention and of pharmaceutical preparations which contain the active compound according to the invention in medicine for the treatment of one of the above mentioned illnesses.

The active compound or the pharmaceutical preparations containing said active compound can be administered locally, topically, orally, parenterally, intraperitoneally and/or rectally, preferably, parenterally, especially intraveneously.

In general it has proved advantageous to administer the active compound according to the invention in amounts of about 0.1 to about 300 mg/kg of body weight every 24 hours optionally in the form of several individual administrations, in order to achieve the desired results. Preferred dosages are 20–200 mg/kg for oral application, 0.1–10 mg/kg for intraveneous application and 10–100 mg/kg for other parenteral applications.

However, it can be necessary to deviate from the dosages mentioned and in particular to do so as a function of the nature and body weight of the subject to be treated, the nature and the severity of the illness, the nature of the preparation and of the administration of the medicine, and the time or interval over which the administration takes place. Thus it can suffice in some cases to manage with less than the abovementioned amount of active compound, whilst in other cases the abovementioned amount of active compound must be exceeded.

The particular required optimum dosage and the type of administration of the active compounds can easily be decided by anyone skilled in the art, on the basis of his expert knowledge.

In the following text, experiments to investigate and evaluate the antiviral activity are described.

EXAMPLE A

Cell culture experiments

In cell cultures, which are infected with herpes simplex or cytomegalovirus, pronounced cytopathic effects occur a few days after infection. It was possible greatly to reduce or prevent the occurrence of these cytopathic effects by treating the infected cell cultures with the compound of the formula (I) (also compare Preparation Example 1).

1. Treatment of L-929 cells which have been infected with herpes simplex virus

L-929 cells of the mouse from Flow Laboratories, D-5309 Meckenheim, were cultured in Roux bottles by the method of Dulbecco and Vogt (Proc. Nat. Acad. Sci. USA 38, 376 (1952)). Each Roux bottle contained $1 \times 10^8$ cells. After the cells had formed a continuous layer, the culture medium was removed. The cells were infected with 5 ml of a virus suspension containing $3 \times 10^6$ plaque-forming units (Dulbecco and Vogt: *J. exp. Med.* 99, 167, 1954) and the test substance at a concentration which was not cytotoxic. After an adsorption time of 1 hour, 50 ml of culture medium containing test substance were added to each culture bottle. The extent of cell destruction due to the virus in the treated and untreated Roux bottles was determined by microscopy at the stated time. The typical cytopathic effect which is produced after infection of cells with herpes simplex virus is inhibited in cultures infected and treated with the compound of the formula (I) and the content of infectious virus is reduced.

2. Treatment of mouse embryo fibroblasts which are infected with cytomegalovirus Mouse embryo fibroblasts were cultured in Roux bottles by known procedures (J. Paul: Zell- und Gewebekulturen (Cell and tissue cultures), Berlin 1980, page 187). Each Roux bottle contained $2 \times 10^7$ cells. After the cells had formed a continuous layer, the culture medium was removed. The cells were infected with 5 ml of a virus suspension containing $3.7 \times 10^6$ plaque-forming units (Dulbecco and Vogt: *J. Exp. Med.* 99, 167, 1954) and the test substance at a concentration which was not cytotoxic. After an adsorption time of 1.5 hours, 50 ml of culture medium containing test substance was added to each culture bottle. The extent of cell destruction due to the virus in the treated and untreated Roux bottles was determined by microscopy at the stated time. The typical cytopathic effect which is produced after infection of cells with cytomegalovirus is inhibited in infected cultures treated with the compound of the formula (I) and the content of infectious virus is reduced.

EXAMPLE B

Animal experiment/cutaneous test on guinea pigs

The test was carried out in analogy with the method worked out by Hubler et al. (*J. Invest. Dermatol.* 62, 92–95, (1974). Guinea pigs weighing 500 to 600 g were depilated on the abdomen and anaesthetised with nembutal (15 mg/kg i.p.). Previously marked areas of skin were infected with a multiple vaccination lancet ('vaccination gun'). The virus material used was medium from rabbit kidney cells which had been infected with herpes simplex virus type I. Treatment can be local, parenteral, oral, intraperitoneal or intravenous. The controls used were infected animals which were untreated or treated with placebo. The evaluation was in accordance with the number and size of the herpes vesicles. The results are compiled in the table below.

TABLE

Activity in the cutaneous test on guinea pigs after oral administration

| Dose of active compound (compound I) mg/kg | Guinea pig No. | Days after infection | | | |
|---|---|---|---|---|---|
| | | 2 | 3 | 4 | 5 |
| 0 | 760 | ++<br>++-+++<br>++ | +++<br>+++<br>++ | +-+++<br>++<br>++ | +-+++<br>++-+++<br>++ | ++-+++<br>++<br>++-+++ | +++<br>+++<br>++ | +++<br>++-+++<br>++-+++ | +++<br>+++<br>++-+++ |
| 0 | 761 | +++<br>+++<br>+++ | +++<br>+++<br>++-+++ | +++<br>+-+++<br>++ | +++<br>+++<br>++ | +++<br>++-+++<br>++ | +++<br>+++<br>++ | +++<br>++-+++<br>++-+++ | +++<br>+++<br>+++ |
| 25 | 762 | +<br>0<br>+ | +<br>0<br>+ | +<br>0<br>+ | +<br>0<br>+ | ++-+++<br>+<br>++ | ++<br>+<br>++ | ++<br>+<br>++ | ++<br>+<br>++ |
| 25 | 763 | ++<br>+<br>+ | +<br>+-++<br>+ | +<br>+<br>+ | +<br>+<br>+ | +<br>+<br>+ | +<br>+<br>+ | +<br>+<br>+ | +<br>+<br>+ |

| Dose of active compound (compound I) mg/kg | Guinea pig No. | Days after infection | | | |
|---|---|---|---|---|---|
| | | 6 | 7 | 8 | |
| 0 | 760 | +++<br>++<br>++ | +++<br>++<br>++ | +++<br>++<br>++ | +++<br>++ | scab formation and shedding of scabs |
| 0 | 761 | +++<br>++-+++<br>++-+++ | +++<br>+++<br>++-+++ | +++<br>++-+++<br>++ | +++<br>+++<br>++ | scab formation and shedding of scabs |
| 25 | 762 | ++<br>+<br>++ | +<br>+<br>++ | scab formation and shedding of scabs | | |
| 25 | 763 | Scab formation and shedding of scabs | | scab formation and shedding of scabs | | |

+ = virus lesions just visible
++ = individual and somewhat larger (>0.5 mm diameter) virus lesions
+++ = several larger virus lesions, some confluent
0 = no lesions

PREPARATION EXAMPLE

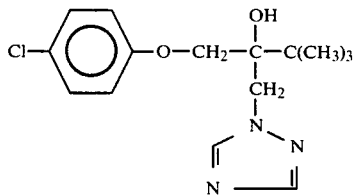

72.15 g (0.3 mol) of 2-(4-chlorophenoxymethyl)-2-tert.-butyloxirane and 24.15 g (0.35 mol) of 1,2,4-triazole in 120 ml of ethanol are heated under reflux for 48 hours. The mixture is then evaporated and the residue is taken up in 200 ml of ethyl acetate and heated. It is then cooled in an ice bath and the solid material is filtered off with suction and washed with ethyl acetate. The filtrate is evaporated, the residue is dissolved in ether/hexane and hydrogen chloride is passed through. The precipitate is filtered off with suction, washed with ether and the free base is obtained by addition of ethyl acetate/1 N sodium hydroxide solution. 60.2 g (65% of theory) of 2-(4-chlorophenoxymethyl)-3,3-dimethyl-1-(1,2,4-triazol-1-yl)-2-butanol of melting point 84° to 87° C. are obtained.

COMPOSITION EXAMPLES

1. Solution

| | |
|---|---|
| Active compound according to formula (I) | 10 g |
| Ethanol, pure, 96% | 300 g |
| Isopropylmyristate | 526 g |
| | 836 g |

2. Cream

| | |
|---|---|
| Active ingredient according to formula (I) | 10 g |
| Sorbitan-monostearate | 20 g |
| Polyoxyethylene(20)-sorbitan-monostearate | 15 g |
| Sparmaceti, artificial | 30 g |
| Mixture of Cetyl- and Stearylalcohol | 100 g |
| 2-Octyldodecanol | 135 g |
| Benzylalcohol | 10 g |
| Water, demineralised | 680 g |
| | 1000 g |

What is claimed is:

1. A method for treating a warm-blooded animal suffering from the effects of herpes simplex virus or cytomegalo virus which comprises administering to said warm-blooded animals an effective anti-herpes simplex or an effective anti-herpes cytomegalo amount of 2-(4-chlorophenoxymethyl)-3,3-dimethyl-1-(1,2,4-triazol-1-yl)-2-butanol.

2. A method of claim 1 wherein administration is effected orally.

3. A method of claim 1 wherein administration is effected parenterally.

4. A method of claim 1 wherein administration is effected topically.

5. A method of claim 1 wherein the virus being treated is herpes cytomegalo virus.

* * * * *